(12) United States Patent
Solo De Zaldivar et al.

(10) Patent No.: US 8,373,232 B2
(45) Date of Patent: Feb. 12, 2013

(54) DEVICE TO DETECT AND MEASURE STATIC ELECTRIC CHARGE

(75) Inventors: José Solo De Zaldivar, Wädenswill (CH); Philip John Poole, Mühlehorn (CH)

(73) Assignee: Microdul AG, Zürich (CH)

( * ) Notice: Subject to any disclaimer, the term of this patent is extended or adjusted under 35 U.S.C. 154(b) by 345 days.

(21) Appl. No.: 12/873,531

(22) Filed: Sep. 1, 2010

(65) Prior Publication Data

US 2011/0049586 A1  Mar. 3, 2011

(30) Foreign Application Priority Data

Sep. 2, 2009 (EP) ..................................... 09169252

(51) Int. Cl.
*H01L 23/62* (2006.01)
*G01R 29/12* (2006.01)

(52) U.S. Cl. . 257/356; 257/360; 257/364; 257/E29.015; 324/458

(58) Field of Classification Search .................. 257/356, 257/360, 364, E29.015; 324/458
See application file for complete search history.

(56) References Cited

U.S. PATENT DOCUMENTS

| | | | |
|---|---|---|---|
| 4,007,418 A | 2/1977 | Hanna | |
| 4,084,134 A | 4/1978 | Nagano | |
| 4,100,484 A | 7/1978 | Buchheit | |
| 4,370,616 A | 1/1983 | Williams | |
| 5,315,254 A | 5/1994 | Wang et al. | |
| 5,376,879 A | 12/1994 | Schrimpf et al. | |
| 6,137,338 A * | 10/2000 | Marum et al. | 327/318 |
| 6,462,552 B1 | 10/2002 | Suzuki | |
| 2002/0063562 A1 | 5/2002 | Werner, Jr. | |

* cited by examiner

*Primary Examiner* — Minh-Loan T Tran
(74) *Attorney, Agent, or Firm* — The Webb Law Firm

(57) ABSTRACT

A device (10) to detect and measure static electric charge (q) on an object (100) being positioned in a distance (r.) from an input electrode (11) of the device (10) comprises at least one MOS field transistor (20). The input electrode (11) is connected with the gate electrode (21) of the MOS-FET (20) to detect said electrical charge. The MOS-FET (20) can comprise a gate oxide layer underneath the gate (21) and over the source (22) and drain (23) areas having a sufficient thickness to allow the MOS field transistor (20) to withstand several kilovolts (kV) of voltage and to avoid the loss of charges by tunnel effect due to the high potential of the gate electrode during ESD events.

12 Claims, 5 Drawing Sheets

DEVICE TO DETECT AND MEASURE STATIC ELECTRIC CHARGE

TECHNICAL FIELD

The present invention relates to a device to detect and measure static electric charge on an object being positioned in a distance from an input electrode of the device; according to the preamble of claim 1.

PRIOR ART

Such a device is known from U.S. Pat. No. 5,315,254. The apparatus makes the measurement with the object being positioned in a so-called safe distance from the apparatus acknowledging problems connected with electrostatic discharge events.

A device showing the features of the preamble of claim 1 is shown in US 2002/0063562. Said device is capable to generate a low voltage electrical signal in response to a signal from a sensing electrode. The device uses an occluder to modulate the signal of the sensing electrode and is not capable to sense the charge of a charged object without use of such a modulator. The transistors used operate in the range of 1700 Volts and is protected with a Zener diode against damage from overvoltage. Since there is a diode connected to the gate it will be impossible to detect static charges from a charged object in the proximity of the input electrode.

A further similar device is shown in U.S. Pat. No. 4,084,134 connecting the probe with a field effect transistor. The probe is also connected via a high input resistor to the battery, protecting the device in case of a high voltage charge. The device detects a voltage difference between a conductor at a certain potential and earth. It is incapable to detect a static charged non-conducting material.

Electrostatic discharge (ESD) is a physical phenomenon that takes place when objects are electrically charged. Charging takes place when two objects of different materials, each with different electron affinity, are brought together or taken apart, resulting in a change in charge by electron migration from one material to another. Due to this effect large voltages in the order of kilovolts can build up prior to discharge.

The destruction of electronic devices by ESD events still produces significant losses in the microelectronic industry. Hazardous ESD events causing costly failures can occur during wafer processing, testing, bonding and packaging of ICs as well as during production of electronic modules.

The continuous increase in packing density, decreasing geometries of internal components within an IC and the thinner gate dielectric layers used in the production of advanced CMOS processes make IC chips more and more sensitive to electrostatic discharge.

The prevention of ESD events in electrostatic protected areas within the production chain of microelectronic devices requires a significant effort in terms of implementing anti-static precautions relating to people, devices, packages, machines, materials, methods, environment and training.

Despite the tremendous effort made in the semiconductor industry to protect devices from ESD destruction, ESD remains a critical issue. It is therefore important to be able to continuously monitor and measure the level of electrostatic charge on people, machines and electronic instruments within the manufacturing areas of semiconductor and microelectronic factories.

SUMMARY OF THE INVENTION

It is therefore an object of the present invention to provide a cheap and efficient device for continuously monitoring electrostatic charges generated in production environments.

The invention describes the concept, principle and construction of an electronic device according to the preamble of claim 1 able to detect electric charges. Such a device is called an ESCM (Electrostatic charge monitor).

The ESCM presented in this paper is in essence an electronic contactless electroscope that is battery powered, has very small dimensions, and is light and therefore easily portable. The ESCM can be assembled into packages of a few cubic centimeters volume and could therefore be made smaller than a pencil.

Electrostatic charge is present wherever static charge can accumulate for any reason. The accumulation of charge may take place on a surface (e.g. a coat) or within a volume (e.g. air). The device according to the invention detects this charge directly using a MOS transistor gate. The invention is not only able to detect the presence of charge but also to determine if it poses a danger to electronics. The device will only react if electrical charge is collected at the gate. It will not react to a pure change in capacitance attached to the gate. The transistor used in the device is protected by using a thick (1 to 2 micrometer) gate dielectric layer ($SiO_2$).

It is a further advantage of the device according to the invention, that, if no charge is present, the transistor in the ESCM is OFF and no current through the source-drain flows. If no current flows then no battery power is consumed. Additional components to signal the presence of charge, such as an LED or piezo-acoustical device are preferably designed such that they are only activated when the detecting MOS transistor is ON. It is possible to have no current flow in the device unless charge is present. An example of an embodiment using these features is given in FIG. 3. This circuit is able to detect positive and negative charges. In order to do this there are two input MOS transistors one n-channel and the other one p-channel. Positive charged objects will switch ON the n-ch MOS and negative charged objects will switch ON the p-ch device.

Beside the oxide thickness of the $SiO_2$ layer, the device according to the inventions comprises a direct connection between input electrode and the gate is direct and in that said low resistance has no further connection with the device having a lower resistance than the impedance provided by the gate oxide layer connection within the MOS transistor 20.

Further embodiments of the invention are laid down in the dependent claims.

The ESCM according to the invention has the following advantages with respect to other detectors within prior art: It is very simple and a low cost construction. The device allows low voltage battery operation. The device has very low power consumption (i.e. only when a charge is detected). The device can be fitted in a housing with very small dimensions which enhances portability. The concept of the device allows the generated ESD voltage to be determined quantitatively. The device is very reliable due to simplicity. The field transistors used can be manufactured using most of the existing CMOS technologies. The device detects electrostatic charged objects without the need to touch them. The principle of charge detection is purely static. The electric field produced by the charged object does not need to be converted into an alternating signal. This would in general increase the complexity, power consumption, volume, etc. of the device. Because the detection principle of charges is purely static the device does not influence the charged object which will keep the initial amount of charge as long it is not touched by the detector. The charge induced on the transistor gate will remain even if the charged object is separated from the detector due to the very high input resistance of the device.

The device can be used for the following not limiting list of applications:

- As a portable alarm for operators in electronic assembly areas.
- As an ESD alarm system for assembly equipment of electronic components.
- As an ESD alarm system for semiconductors production equipment.
- As an ESD alarm for wafer testing equipment.
- In areas where electrostatic discharges could produce fire and explosions of explosive materials.
- To survey critical points within electrostatic protected areas.
- In chemistry labs working with inflammable materials.
- As ESD alarm system for cars or other vehicles susceptible to be electrostatic charged.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
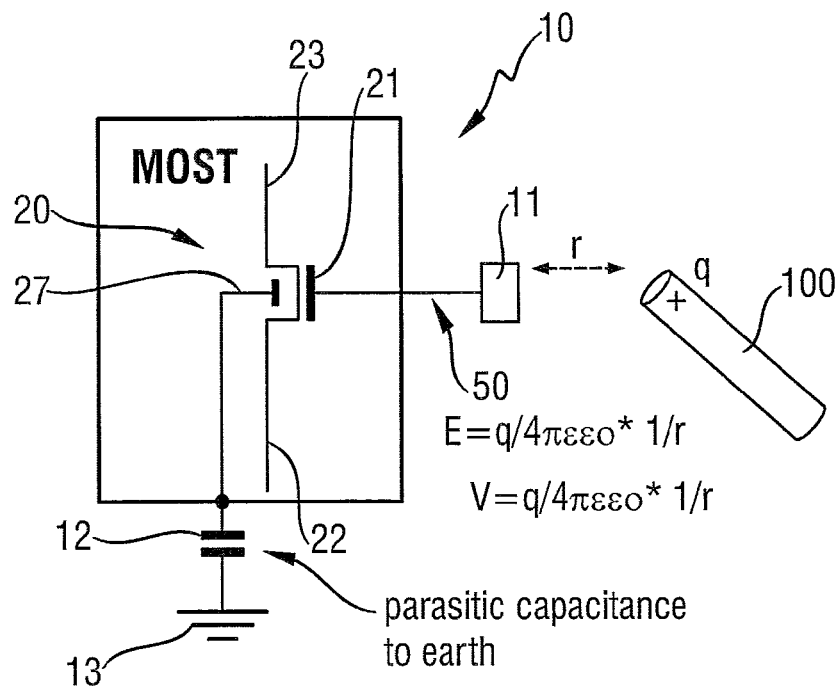
FIG. 1 shows the physical principle of the device according to the invention in front of a charged object positioned in a distance from the device.

FIG. 1 shows the physical principle of the ESCM (Electrostatic charge monitor) 10 according to the invention in front of an object 100 with a charge q, being positioned in a distance r from device 10.

The ESCM is an electronic device 10 able to detect positive and negative charged objects. Any charged object 100 put in the vicinity (distance r) of the ESCM will induce an electric field and this in turn will produce an increase in the potential of the input electrode 11 of the ESCM. The physical principle of operation is based on charging of the gate electrode 21 of a MOS transistor 20. The amount of charge induced on the gate electrode will be Vgs*Cox, where the Cox is the gate electrode capacitance. When a charged object 100 approaches—via the electrode 11—the gate 21 of the MOS transistor 20, the potential of the gate 21 will change due to the electrical field produced by the charged object 100. In principle, the input electrode can consist of any conducting material. The size of the electrode is not very significant if the ESCM is being used merely as a charge detector. If the ESCM is being used to measure electrostatic potential then the size must be taken into account when calibrating the device.

The change in the potential of the gate electrode 21 of the transistor 20 will create a conducting channel between the source 22 and the drain 23 of the MOS transistor 20 thus switching it ON.

Based on this principle it is possible to construct a device 10 able to indicate whether an object 100 placed in its proximity is electrically charged.

In other words, when a charged object 100 approaches the gate 21 of the MOS transistor 20, charges will be induced on the gate 21 of the transistor 20 and, as result, the transistor channel area will become inverted. The device 10 is then turned ON and a current will flow between the drain 23 and the source 22 of the transistor 20. The gate electrode is completely isolated from the rest of the circuit. There is no significant energy transfer from the gate to another part of the circuit. The energy needed to switch a LED or/and an acoustic device is given by a small battery.

Fundamental precautions must be taken in the design of a MOS transistor capable of detecting electrostatic charges to avoid its destruction. The layout, structure and technology used to produce a special MOS transistor are essential ideas of this novel method for electrostatic charge detection.

It is acknowledged that all conventional MOS-transistors fabricated in CMOS technology cannot be used for the detection of electrostatic charged objects 100 since the high electrical potential induced on the gate 21 will destroy the gate dielectric ($SiO_2$) layer. This type of ESD damage results in a short circuit between the gate 21 and the source 22, drain 23 or substrate 26.

The gate electrode 21 of the transistor has to be floating in order to collect sufficient charge from the charged object 100. In addition, the input path from the input electrode 11 to the gate electrode of the transistor 21 must have a very high resistance (>=1 to $5*10^{13}$ Ohm) to the substrate, source and drain of the transistor in order to minimise the loss of charges induced on the gate electrode and therefore special design considerations are required for the input transistors. In other words, the connection between the input electrode 11 and the gate electrode 21 is a direct and low resistance connection 50. Said low resistance connection 50 has no further connection with the device having a lower resistance than the resistance provided by the gate oxide layer 24 underneath the gate electrode of the MOS transistor.

Diodes or transistors cannot be used to protect the dielectric gate as the leakage currents would dissipate the induced charge and inhibit gate potential. The device according to the invention uses a MOS-transistor with a very thick gate oxide layer in the order of microns. Preferably the thickness is between 1 and 2 micrometers. This is due to two reasons: The gate dielectric layer has to withstand several kilovolts (kV) of voltage. Secondly, the charge accumulated in the gate electrode has to be kept there to make the transistor conducting. In case the gate dielectric would be much thinner, the large electric field across the gate dielectric will inject electrons by tunneling through the dielectric gate layer and discharge the gate electrode so that the transistor will not switch ON.

The thickness of the gate oxide is chosen such that the gate 21 can withstand several kilovolts (kV) of voltage.

Figure 2:
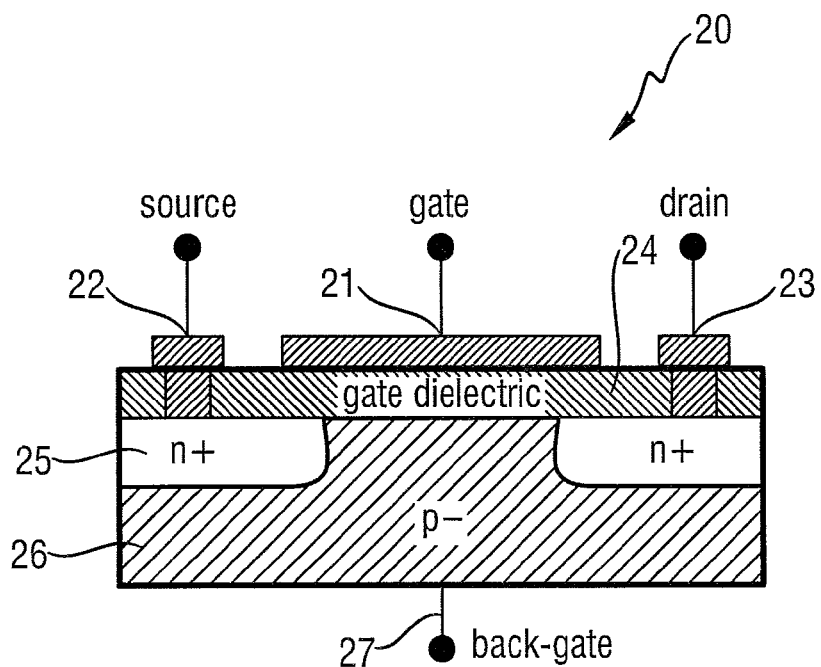
FIG. 2 shows the cross section of an n-ch MOS transistor used in a device according to the invention.

FIG. 2 shows a cross-section of the MOS (metal oxide semiconductor) field-effect transistor 20 according to FIG. 1, more specifically; it shows the cross section of an n-ch MOS transistor 20. The gate electrode 21 lies on a thick oxide layer 24 of about 1 to 2 μm thickness. The thick oxide layer comprises of silicon oxide ($SiO_2$). This transistor is commonly called a "field transistor" in the CMOS technology terminology. A common (active) CMOS transistor on an IC has a thin gate oxide layer (5 nm to 50 nm) which is not suitable for electrostatic charge detection as explained above.

The extra thick (>1.0 micrometers) gate dielectric layer 24 which prevents the destruction of the transistor by ESD events, extends over the substrate 26, the n-doped regions 25 and the corresponding metal contacts for source 22 and drain 23. The substrate 26 is then connected to the back-gate 27, which, in the case of FIG. 1, is connected via a parasitic capacitance 12 to earth 13.

It is possible for someone skilled in the art to prepare such dedicated field transistors in a conventional CMOS technology. In this sense it is possible to integrate in a single chip a circuitry containing the input field transistors 20 and the high performance transistors (which are the normal MOSTs devices) together. This makes the construction of monolithic charge detection devices (ICs) with different complexity and applications possible. This is a big advantage because it is not necessary to have special technologies in a wafer factory.

Figure 3:
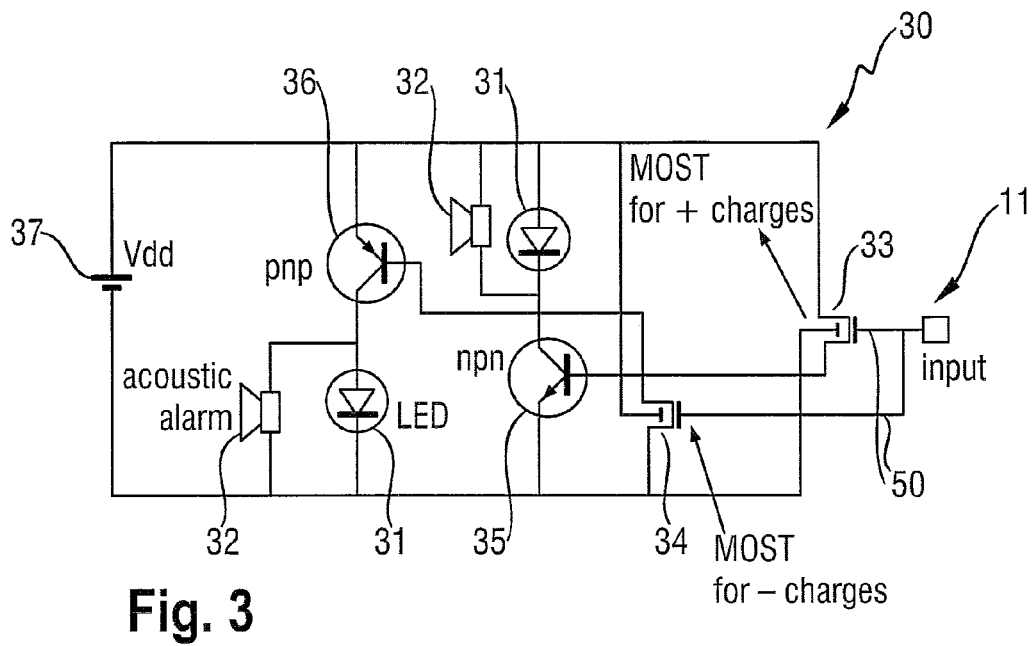
FIG. 3 shows an embodiment of a device layout according to the invention using a transistor according to FIG. 2.

FIG. 3 shows an embodiment of a device according to the invention using a transistor according to FIG. 2. The operation of the ECSM according to FIG. 3 is now explained, wherein such a contactless electroscope can be used for monitoring the electrostatic charge state of any particular object. The object can be the human body, a machine, a tool or an electronic component. The ESCM 30 in the embodiment presented in FIG. 3 is a simple construction, just having a LED 31 and an acoustic alarm 32, that are switched ON to indicate the proximity of a charged object in the vicinity of the input 11. In other words, the drain 23 of the MOS field transistor 33, 34 is connected to such charge reporting elements 31, 32 having a current consumption only when a charge is detected.

The threshold voltage at which the LED 31 is turned-on can be adjusted by adding external components (capacitors) in the input circuitry of the monitor module.

In practice the threshold voltage of the device should be set to between 50 to 100V. The range of operation is 50 to 1500V. The ESD monitor 30 must be designed such that it survives discharges up to 2000V according to the human body (HBM) ESD model (JESD22-A114-B) or 200V according to the machine (MM) ESD model (JESD-A115-A), standards provided by JEDEC.

The embodiment according to FIG. 3 comprises two input transistors 33 and 34 according to FIG. 2, wherein their gates are connected to input 11. One input transistor 33 is provided to detect positive charges. The other input transistor 34 is provided to detect negative charges. Once the input transistor 33 or 34 of the ESCM is turned ON due to the detection of a electrostatic charge, the signal from the drain of the transistor can be used for different purposes: For instance an optical or/and an acoustic device could be switched ON. FIG. 3 shows an example of such a circuitry using bipolar transistors 35 and 36 to switch an LED 32 and acoustic components 31, respectively.

It is noted that a simple battery 37 can provide the necessary power supply for the device 30, e.g. a 3V-battery.

Figure 4:
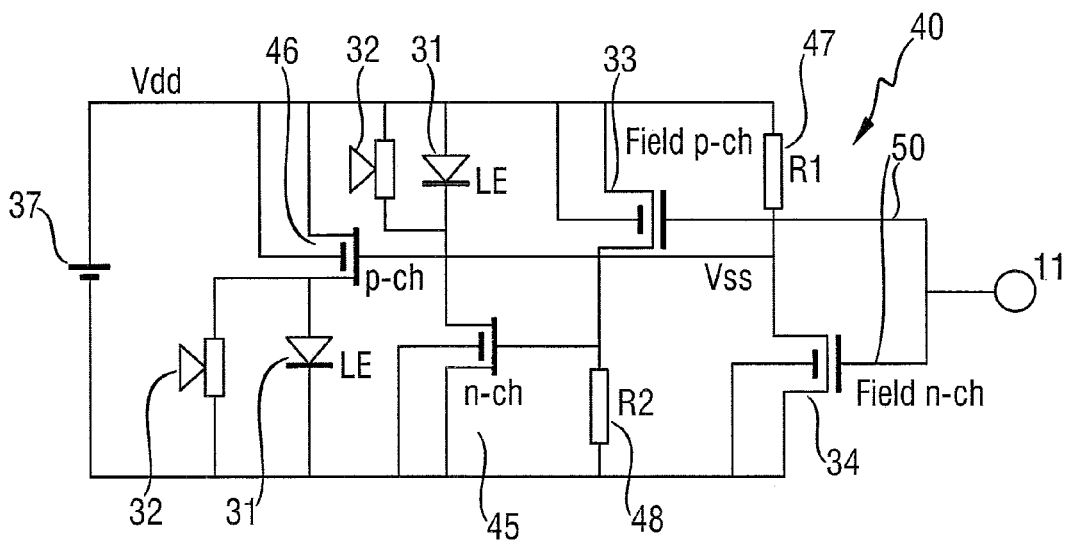
FIG. 4 shows a further embodiment of a device using only MOS transistors.

FIG. 4 shows an embodiment of a device 40 using only MOS transistors. In order to be able to detect positive and negative charges both n-ch and p-ch MOS field transistors are needed at the input of the detector.

When a positively charged object approaches the input 11, the n-ch MOS field effect transistor 34 is turned "ON" and the drain has a voltage close to 0 volts. The gate of p-ch transistor 46 is connected to the drain of the n-ch field transistor 34. Transistor 46 is consequently turned "ON" and a current flows through it to the LED 31 and the acoustic alarm 32. The p-ch MOS field transistor 33 is "OFF" and the drain has a voltage of 0 volts caused by the pull-down resistor R2 48. The following transistor 45 will also be "OFF" and no current will flow through the LED and acoustic alarm connected to it. Similarly when a negatively charged object approaches the input 11, the p-ch field transistor 33 is turned "ON" and consequently the LED 31 and acoustic alarm 32 connected to transistor 45 will be active. When no charge is near the input 11, the input transistors 33 and 34 will both be "OFF". Consequently, the following transistors 45 and 46 will be off since the resistors R1 and R2 47 and 48 pull the gates "OFF".

Figure 5:
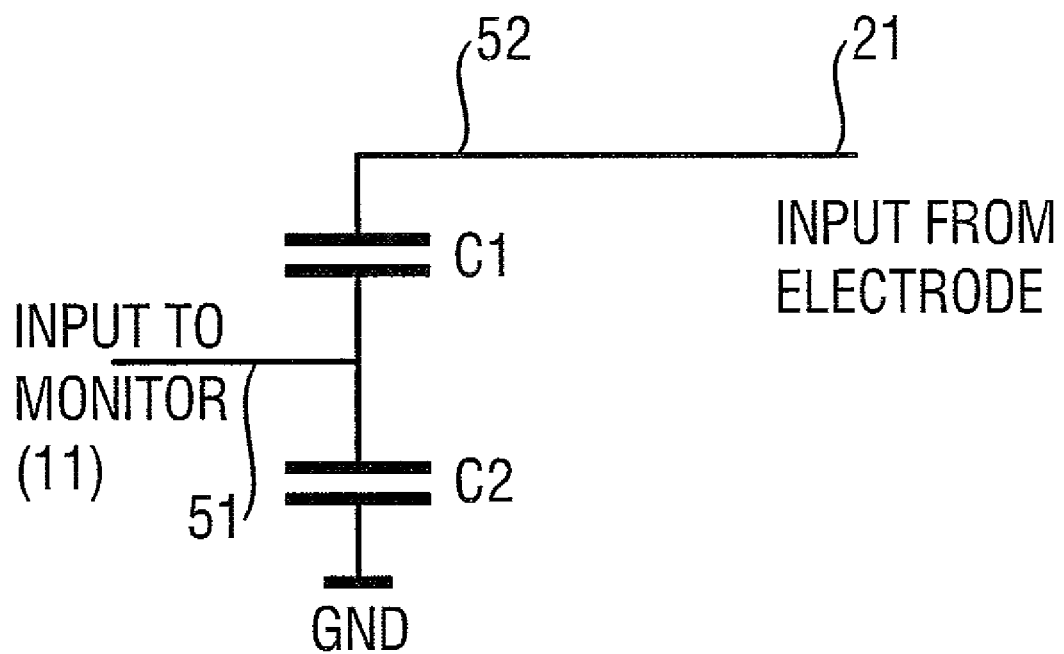
FIG. 5 shows a sensitivity adjusting circuit for a detector according to one of FIGS. 1 to 4.

FIG. 5 shows a sensitivity adjusting circuit for a detector according to one of FIGS. 1 to 4. The sensitivity of a detector according to an embodiment of the invention can be altered by placing a simple capacitive divider 60 on the input 11 as shown in FIG. 5 increasing the electrostatic voltage range that can be measured at the input of the ESC monitor, i.e. the capacitances C1 and C2 are provided between the input electrode 11 and the gate electrode 21 of FIG. 1 or in general the input of device 10, e.g. in front of gate electrodes 33 and 34 of FIG. 3 or 4. The low resistance connection 50 is replaced by a first portion 51 leading from the input electrode 11 to the divider 60, comprising of capacitances C1 and C2, and a second portion 52 leading from one capacitance C1 to the gate 21, wherein the other capacitance C2 is connected with ground.

The extremely high input resistance of the device means that it works even if the back gates 27 of the transistors are not connected to the earth 13. The parasitic capacitance 12 between the device and earth 13 is sufficient to keep the back gates 27 at a very low potential with respect to the high potential of the input. This is an advantage for portable use.

The induced voltage threshold required to trigger the monitor can be adjusted by adding a capacitive divider at the input. However, the use of such a capacitive divider is optional and not mandatory. The device according to the invention may use a capacitive divider to set a threshold.

Figure 6:
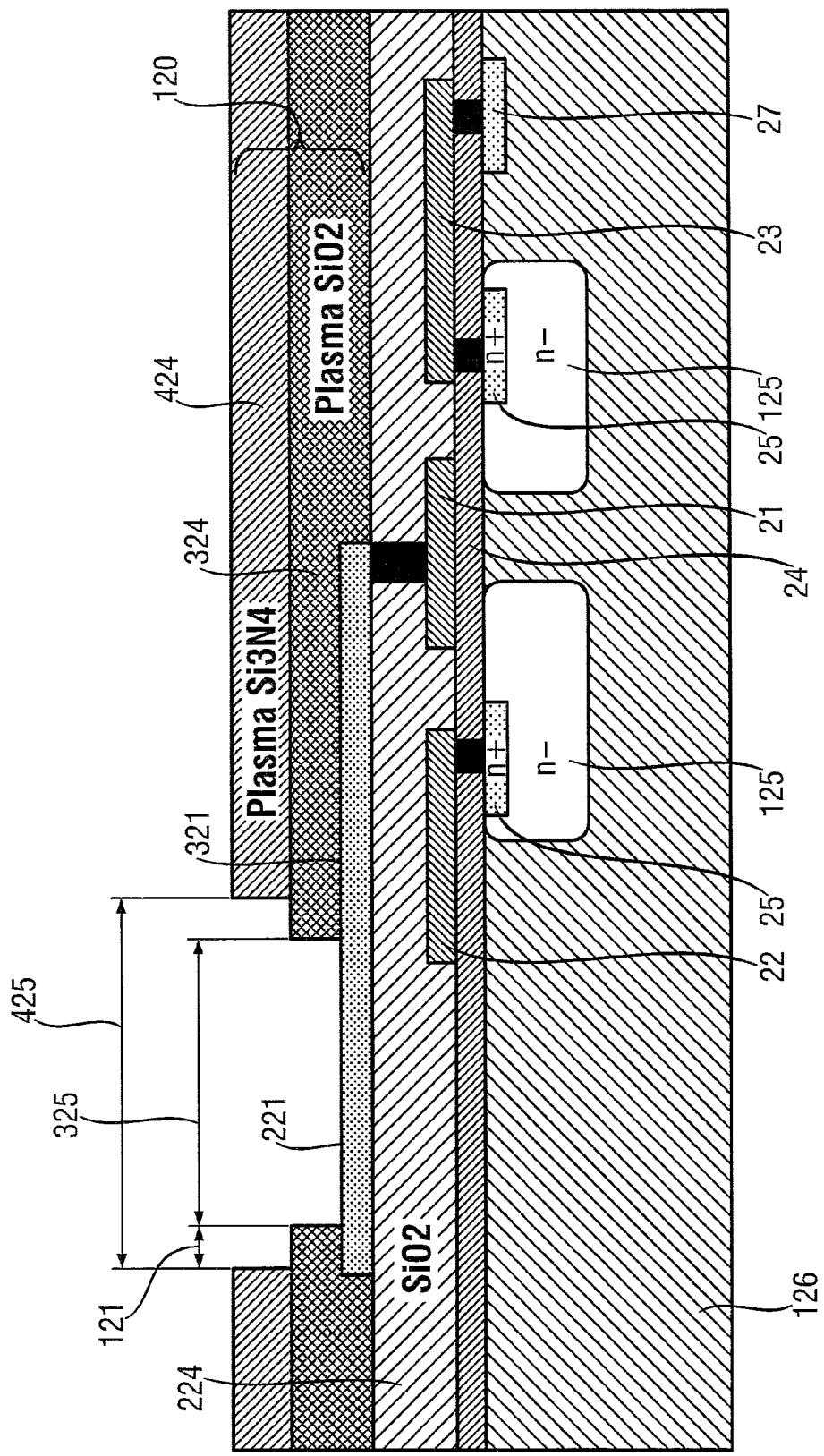
FIG. 6 shows a cross section of the MOS transistor of an embodiment of the device according to the invention having an isolating gate oxide layer in connection with a passivation layer.

FIG. 6 shows a cross section of an n-MOS transistor of the device according to the invention having an isolating gate oxide layer 24 in connection with a passivation layer 120 composed of two layers as explained below. As it was mentioned above, it is important that the connection between the input electrode 11 and the gate 21 has to be very well isolated (specific resistance >$10^{15}$ Ohm*cm) with respect to earth, source and drain of the transistor. Usually the device is covered with a passivation layer 120, being made e.g. of plasma SiN$_3$ and plasma SiO$_2$. The plasma nitride layer 424 has a lower specific resistance ($10^{13}$ Ohm*cm) than the oxide layer ($10^{16}$ Ohm*cm) 324. In order to avoid losing charges from the gate electrode 221, the opening 325 of the passivation nitride layer 120 has to be larger than the opening 425 of the oxide passivation layer 324. If this precaution is not taken leakage currents could be produced between the edge of the nitride layer 424 and the metal pad 221 along the walls of the oxide passivation 324. This effect would discharge the gate electrode 21 and prevent the detection of small amount of charges having a negative impact in the sensitivity of the device. The applicable resistance is calculated as the product of the specific resistance*oxide thickness/area of the gate.

The gate oxide layer 24 is preferably SiO$_2$. However, any dielectric can be used, having a resistivity in the range of and preferably larger than $10^{16}$ Ohm*cm. The oxide layer 324 isolating the gate connection 321 from the environment is also called an additional isolating passivation layer 324, which is covered with a nitride passivation layer 424.

Within the p-substrate 126 of the body region there are two n+ doped regions 25 embedded in n– wells 125. The thick SiO$_2$ layer 24 separates the substrate and the doped regions from the source 22, gate 21 and drain 23 contacts. The metallic source 22 and drain 23 layer are contacting the doped regions 25 through the SiO$_2$ layer 24. These three contacts are isolated via a thick IML or intermediate SiO$_2$ layer 224, also called an intermediate isolation layer, wherein a connection is provided towards the metallic layer 321 leading to a gate contact pad 221. The metallic layer 321 is protected with an additional plasma SiO$_2$ layer 324 and finally covered with the uppermost passivation layer 424, usually a Si$_3$N$_4$ layer. This layer 424 is used to protect the transistor from Na+ contamination and H$_2$O diffusion form the outside. There is an offset 121 between the Si$_3$N$_4$ passivation layer 424 and the SiO$_2$ passivation layer 324 (e.g. of between 5 to 15 micrometer, preferably 10 to 15 micrometer) avoiding a leakage between the metal pad and the Si$_3$N$_4$ layer, which is not a perfect isolator as mentioned before. By introducing the spacing 121 the separation between the nitride layer 424 and the pad surface 221 is increased so that the resistance between both is also increased. The thickness of the intermediate SiO$_2$ 224 as well as the thickness of the additional plasma SiO$_2$ passivation layer 324 is sufficient to prevent any leakage through these layers. Layer thickness for the layer 224 can be chosen e.g. between 1 and 4 micrometers, preferably between 2 and 3 micrometer. Layer thickness for the layer 324 can be chosen e.g. between 0.5 and 1 micrometer. The thickness of the Si$_3$N$_4$ passivation layer 424 is chosen by the man skilled in the art, usually 0.5 to 1.0 micrometers.

Figure 7:
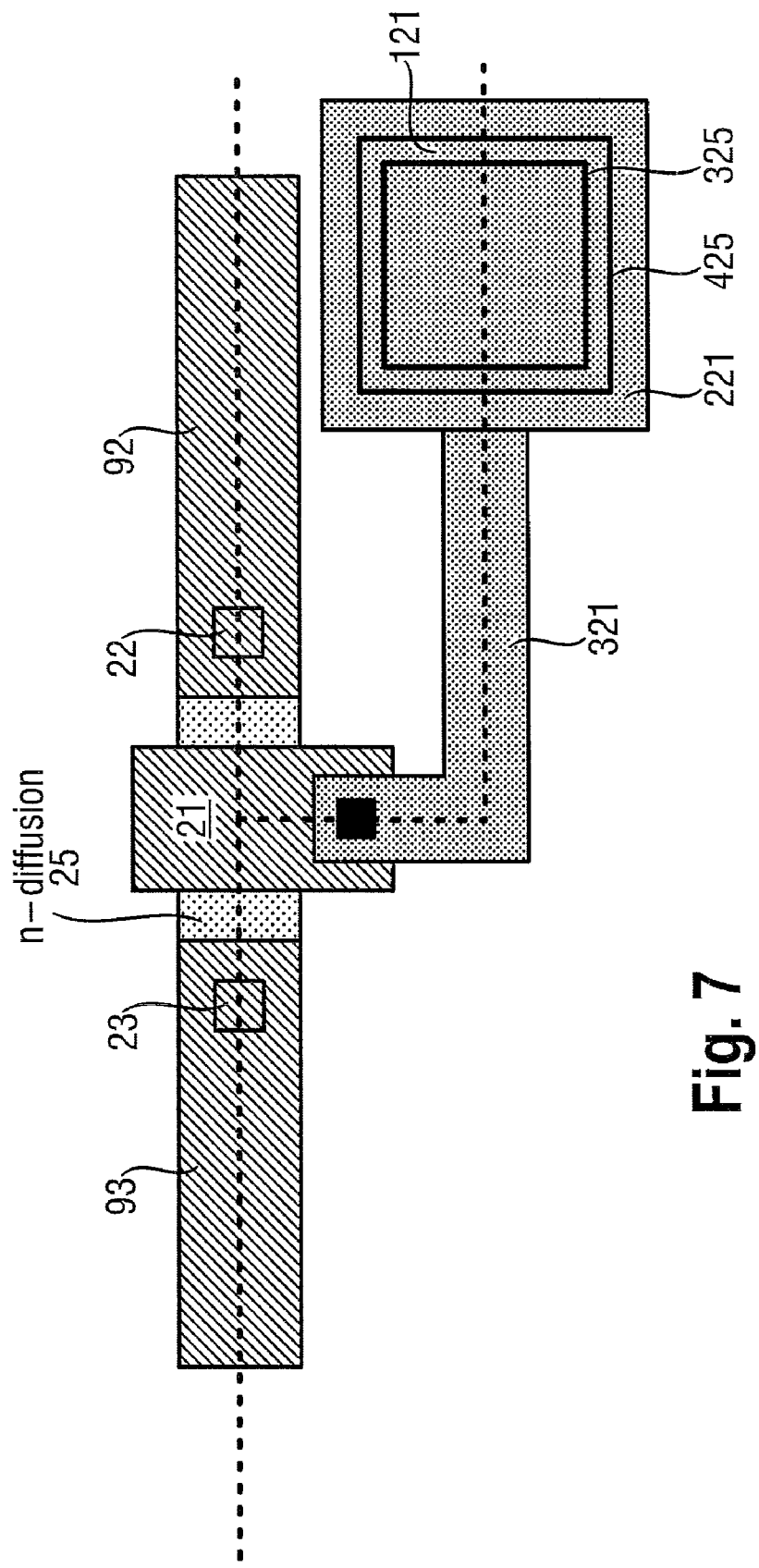
FIG. 7 shows a schematic view on specific layers of the device according to FIG. 6.

FIG. 7 shows a schematic view on the specific layers of the device according to FIG. 6 without showing the passivation and isolating layers. The gate contact 21 below the intermediate SiO$_2$ layer 224 is well protected against any leakage. The source 22 and drain 23 contacts usually comprise metallic lines 92 and 93 for further connections, here in a view from above perpendicular to the gate contact 21. This contact 21 is connected through the SiO$_2$ layer 224 onto said layer 224 and connected via line 321 to the gate pad 221, wherein both metallic elements are provided on said SiO$_2$ layer 224 and thus protected against any contact with the circuitry on the substrate 126. However, it has also to be connected with the outside and to be protected against leakage through the passivation layers 324 and 424. Therefore the present embodiment chooses the combination according to FIG. 6 of a lower SiO$_2$ isolation layer 324 and an upper Si$_3$N$_4$ passivation layer 424 having a gap 121 avoiding leakage between the pad 221 and the Si$_3$N$_4$ layer 424. The two squares shown in FIG. 7 relate to the opening 425 of the nitride layer 424 and the opening 325 of the oxide layer 324.

The transistor shown in the drawings is the special thick gate oxide transistor called field transistor.

The invention claimed is:

1. A device to detect and measure static electric charge on an object positioned at a distance from the device, comprising:
at least one MOS transistor having
a gate electrode;
a source electrode;
a drain electrode;
a gate oxide layer having a thickness of more than 1 micrometer; and
an input electrode directly connected to the gate electrode by a low resistance connection,
wherein the gate oxide layer is positioned underneath the gate and over the source electrode and the drain electrode,
the input electrode of the device is connected with the gate electrode of the at least one MOS transistor to detect said static electric charge, and
the low resistance connection has no further connection with the device having a lower resistance than the resistance provided by a gate oxide layer connection within the MOS transistor.

2. The device according to claim 1, wherein the thickness of the gate oxide layer is between 1.3 and 3 micrometer.

3. The device according to claim 2, wherein the thickness of the gate oxide layer is between 1.3 and 2 micrometer.

4. The device according to claim 1, wherein the gate oxide layer is SiO$_2$.

5. The device according to claim 1, wherein the gate oxide layer is a dielectric having a resistivity larger than $10^{16}$ Ohm*cm.

6. The device according to claim 1, further comprising charge reporting elements being adapted to provide optical and acoustic reporting signals.

7. The device according to claim 6, wherein the charge reporting elements are a LED and a loudspeaker, respectively.

8. The device according to claim 7, further comprising a battery as power supply.

9. The device according to claim 1, further comprising a sensitivity adjustment circuit.

10. The device according to claim 9, wherein the sensitivity adjustment circuit comprises a combination of capacitances connected to an input of the at least one MOS transistor.

11. The device according to claim 1, further comprising an intermediate isolation layer having a gate pad,
wherein the gate electrode, the drain electrode, and the source electrode are covered by said intermediate isolation layer,
the gate electrode is connected to the gate pad on said intermediate isolation layer to be connected with the input electrode, and
the connection between the gate electrode and the gate pad is isolated with an additional isolating passivation layer covered with a nitride passivation layer.

12. The device according to claim 11, wherein an offset is provided between the nitride passivation layer and the additional passivation layer avoiding leakage between the passivation layer and the gate pad.

* * * * *